US012599785B2

(12) United States Patent　　　　　(10) Patent No.:　US 12,599,785 B2
Ferraro et al.　　　　　　　　　　　　(45) Date of Patent:　　Apr. 14, 2026

(54) STEREOTACTIC DEVICE WEARABLE BY A PATIENT FOR LOW-INTENSITY FOCUSED-ULTRASOUND NEUROMODULATION

(71) Applicants: Fondazione I.R.C.C.S. Istituto Neurologico "Carlo Besta", Milan (IT); Istituto Nazionale di Ricerca Metrologica (I.N.RI.M.), Turin (IT)

(72) Inventors: Stefania Ferraro, Chengdu (CN); Giovanni Durando, Turin (IT); Francesco Prada, Milan (IT); Anna Nigri, Milan (IT); Maria Grazia Bruzzone, Milan (IT); Domenico Aquino, Milan (IT); Maria Luisa Fumagalli, Milan (IT)

(73) Assignees: FONDAZIONE I.R.C.C.S. ISTITUTO NEUROLOGICO "CARLO BESTA", Milan (IT); ISTITUTO NAZIONALE DI RICERCA METROLOGICA (I.N.RI.M.), Turin (IT)

( * ) Notice: Subject to any disclaimer, the term of this patent is extended or adjusted under 35 U.S.C. 154(b) by 0 days.

(21) Appl. No.: 18/722,088

(22) PCT Filed: Dec. 12, 2022

(86) PCT No.: PCT/IB2022/062074
　　§ 371 (c)(1),
　　(2) Date: Jun. 20, 2024

(87) PCT Pub. No.: WO2023/119054
　　PCT Pub. Date: Jun. 29, 2023

(65) Prior Publication Data
　　US 2025/0058150 A1　　Feb. 20, 2025

(30) Foreign Application Priority Data
　　Dec. 21, 2021　(IT) .......................... 102021000032006

(51) Int. Cl.
　　*A61N 7/00*　　　(2006.01)
　　*A61B 90/10*　　(2016.01)
　　*A61B 90/14*　　(2016.01)

(52) U.S. Cl.
　　CPC ................ *A61N 7/00* (2013.01); *A61B 90/10* (2016.02); *A61B 90/14* (2016.02); *A61N 2007/0026* (2013.01); *A61N 2007/0086* (2013.01)

(58) Field of Classification Search
　　CPC ...... A61N 2007/0026; A61B 90/10–18; A61B 2090/103; A61B 8/085
　　See application file for complete search history.

(56) References Cited

U.S. PATENT DOCUMENTS

2015/0297176 A1* 10/2015 Rincker ................... A61N 7/00
　　　　　　　　　　　　　　　　　　　　　　601/2
2017/0065835 A1* 3/2017 Park ....................... A61B 6/501
　　　　　　　　　　(Continued)

FOREIGN PATENT DOCUMENTS

EP　　　　3597111 B1　　5/2023
EP　　　　3363497 B1　　12/2023
　　　　　　(Continued)

OTHER PUBLICATIONS

International Search Report for International Patent Application No. PCT/IB2022/062074, mailed Mar. 17, 2023.

*Primary Examiner* — Colin T. Sakamoto
(74) *Attorney, Agent, or Firm* — Armstrong Teasdale LLP

(57)　　　　　　　ABSTRACT

A stereotactic device wearable by a patient for low-intensity focused-ultrasound neuromodulation has a support frame shaped to be fitted around a head of the patient, a first movable component having an arched shape and having a first end and a second end engaged with the support frame at respective first and second coupling points. A second movable component has an engagement portion with the
(Continued)

first movable component adapted to allow the second movable component to move integrally with the first movable component and to slide along the first movable component to take a plurality of positions between a first position in which the second movable component is proximal to the first end and a second position in which the second movable component is proximal to the second end. A low-intensity focused-ultrasound neuromodulation module housed in a support portion of the second movable component has a low-intensity focused-ultrasound sonication probe.

13 Claims, 8 Drawing Sheets

(56)  References Cited

U.S. PATENT DOCUMENTS

| | | | |
|---|---|---|---|
| 2020/0000428 A1* | 1/2020 | Kim | A61B 8/4209 |
| 2021/0016113 A1* | 1/2021 | Hunt | A61N 7/00 |

FOREIGN PATENT DOCUMENTS

| | | |
|---|---|---|
| KR | 20180054400 A | 5/2018 |
| WO | 2021011858 A1 | 1/2021 |

* cited by examiner

STEREOTACTIC DEVICE WEARABLE BY A PATIENT FOR LOW-INTENSITY FOCUSED-ULTRASOUND NEUROMODULATION

CROSS-REFERENCE TO RELATED APPLICATIONS

This application is a National Phase application of PCT International Application No. PCT/IB2022/062074, having an International Filing Date of Dec. 12, 2022, which claims priority to Italian Application No. 102021000032006 filed Dec. 21, 2021.

FIELD OF THE INVENTION

The present invention relates to ultrasound brain stimulation techniques, in particular to a stereotactic device wearable by a patient for low-intensity focused-ultrasound neuromodulation.

TECHNOLOGICAL BACKGROUND OF THE INVENTION

Stereotactic devices wearable by a user for low-intensity focused-ultrasound neuromodulation are known.

Such devices typically comprise a frame housable on the patient's head having a complex structure with movable components to allow the low-intensity focused-ultrasound source to be positioned so as to convey the low-intensity focused-ultrasound onto the identified cerebral target to be subjected to neuromodulation.

In addition to the complexity, the structure of these frames is so cumbersome and heavy to undoubtedly represent a considerable inconvenience for the patient.

In addition, such systems do not have optimal neuro-stimulation replicability in the different sessions necessary to achieve the expected benefits.

Furthermore, the structure of the frames of the known devices limits the movements of the low-intensity focused-ultrasound source, allowing only the modulation of some identified cerebral targets, among those potentially known as modulable.

In addition, the modulation systems used by the known devices only allow the modulation of large non-specific regions of the identified cerebral target (with modulations of other regions as well, which should not be modulated), failing to obtain high precision and accuracy in the modulation of the identified targets, especially in the case of deep cerebral targets.

Furthermore, the known devices are only usable in ultra-specialist hospitals since they require, for being used, the presence of highly specialized staff on site who use the system correctly.

In light of the above, the need is strongly felt to provide a stereotactic device comfortably wearable by a user for low-intensity focused-ultrasound neuromodulation, which ensures reaching the target precisely and accurately during the various neuromodulation sessions, which allows reaching the various cerebral targets, even deep and of small dimensions, and which is also usable in non ultra-specialist environments, but always under the control of highly specialized staff.

SUMMARY

It is the object of the present invention to devise, design and provide a stereotactic device wearable by a user for low-intensity focused-ultrasound neuromodulation, which allows overcoming the drawbacks complained of above with reference to the prior art, in particular which is more comfortable for the patient and ensures a precise and accurate positioning of the low-intensity focused-ultrasound source with respect to the target to be subjected to neuromodulation, which reaches all the cerebral targets of greater interest and which is usable in a non ultra-specialist environment.

Such an object is achieved by a stereotactic device as described and claimed herein.

Preferred embodiments of the stereotactic device are also described.

It is further the object of the present invention a low-intensity focused-ultrasound neuromodulation system adapted to employ such a device.

BRIEF DESCRIPTION OF THE DRAWINGS

Further features and advantages of the device according to the invention will become apparent from the following description of preferred exemplary embodiments thereof, given by way of non-limiting indication, with reference to the accompanying drawings, in which.

It should be noted that, in the aforesaid figures, equivalent or similar elements are indicated by the same numeric and/or alphanumeric reference.

DETAILED DESCRIPTION

Figure 1:
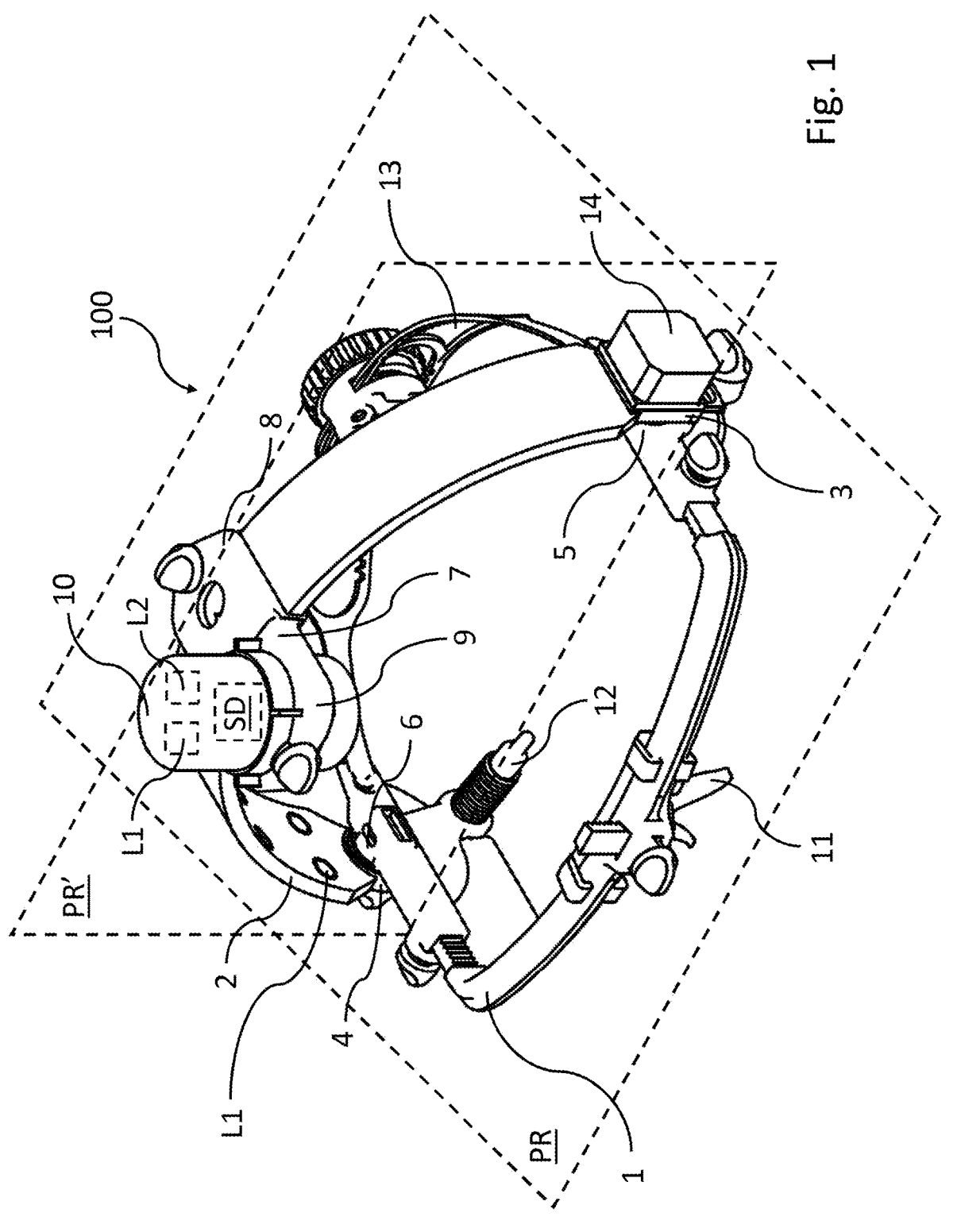
FIG. 1 diagrammatically shows a perspective view of a stereotactic device wearable by a patient for low-intensity focused-ultrasound neuromodulation, according to the present invention.
Figure 2:
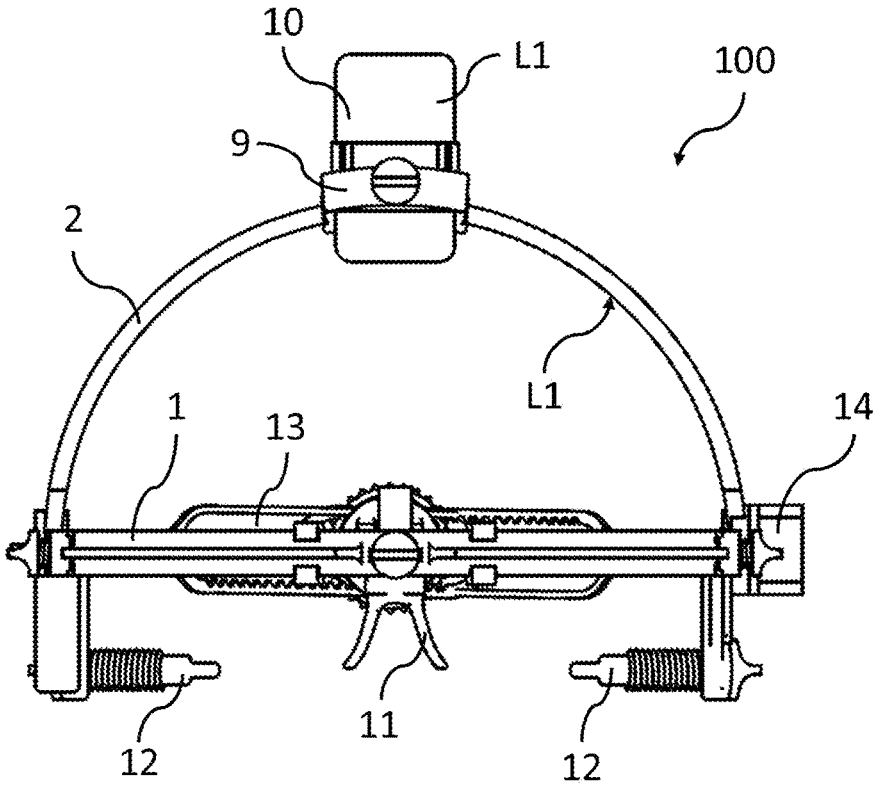
FIG. 2 diagrammatically shows a front view of the stereotactic device for low-intensity focused ultrasonic neuromodulation in FIG. 1.
Figure 3:
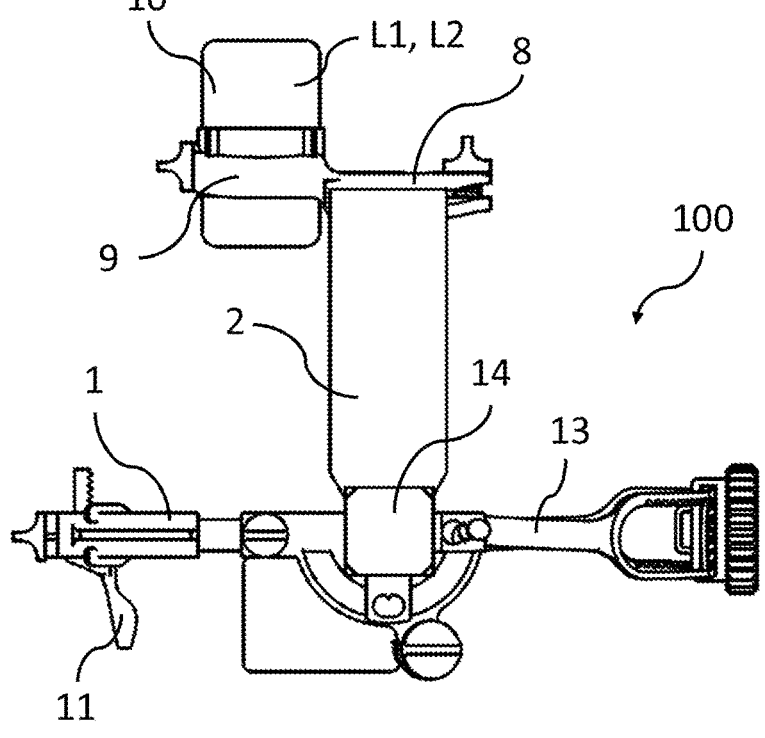
FIG. 3 diagrammatically shows a side view of the stereotactic device for low-intensity focused-ultrasound neuromodulation in FIG. 1.

With reference to the aforesaid figures and in particular to FIGS. 1, 2, 3, 4, 5, 6a, 6b, 7a and 7b, the reference numeral 100 indicates a stereotactic device wearable by a patient for low-intensity focused-ultrasound (LIFU) neuromodulation, hereinafter also referred to as a stereotactic device only, or simply a device.

The device 100 comprises a support frame 1 extending along a first reference plane PR.

The support frame 1 is shaped to be fitted around a head of a patient P.

The device 100 comprises a first movable component 2 with respect to the support frame 1.

The first movable component 2 has a substantially arched shape which extends upwards with respect to the first reference plane PR and lies on a second reference plane PR'.

The first movable component 2 has a first 3 and a second 4 end each respectively engaged with the support frame 1 in a respective first 5 and second 6 coupling point.

The first movable component 2 is adapted to rotate about a rotation axis passing through the first 5 and second 6 coupling points of the support frame 1 to take a plurality of inclined positions with respect to the reference plane PR between a first position in which the first movable component 2 is inclined with respect to the first reference plane PR by a substantially null angle and a second position in which the first movable component 2 is inclined with respect to the first reference plane PR by an angle substantially equal to 180°.

As will also be indicated below with reference to FIG. 8, the device 100 comprises a first servo-assisted motorization unit M1 configured to rotate, as indicated above, the first movable component 2 with respect to the support frame 1.

Referring again to the figures, the device 100 further comprises a second movable component 7 with respect to the first movable component 2.

The second movable component 7 comprises an engagement portion 8 with the first movable component 2 adapted to allow the second movable component 7 to move integrally with the first movable component 2.

The engagement portion 8 of the second movable component 7 with the first movable component 2 is further adapted to allow the second movable component 7 to slide along the first movable component 2 so as to take a plurality of positions between a first position in which the second movable component 7 is proximal to the first end 3 of the first movable component 2 and a second position in which the second movable component 7 is proximal to the second end 4 of the first movable component 2.

In this regard, the device 100 comprises a second servo-assisted motorization unit M2 (also diagrammatically shown in FIG. 8) configured to slide the second movable component 7 along the first movable component 2.

Referring again to the figures, the second movable component 7 further comprises a support portion 9 integral with the engagement portion 8.

The support portion 9 extends away from the first movable component 2 transversely to the second reference plane PR' on which the substantially arched shape of the first movable component 2 lies.

The device 100 further comprises a low-intensity focused-ultrasound neuromodulation module 10 housed in the support portion 9 of the second movable component 7.

The low-intensity focused-ultrasound neuromodulation module 10, during the sliding of the second movable component 7 along the first movable component 2, is adapted to take a plurality of operating positions between a first operating position when the second movable component 7 is proximal to the first end 3 of the first movable component 2 and a second operating position when the second movable component 7 is proximal to the second end 4 of the first movable component 2.

The low-intensity focused-ultrasound neuromodulation module 10 comprises at least one low-intensity focused-ultrasound sonication probe SD.

The at least one low-intensity focused-ultrasound sonication probe SD is for example: a mono-ceramic focused-ultrasound transducer (FUS transducer) for stimulating cerebral targets having a set size greater than 1 $cm^3$; or a pulsed wave multiarray ultrasound transducer (FUS-pulsed wave transducer) for stimulating cerebral targets having a set size less than 1 $cm^3$.

It should be noted that the settings of insonation, pressure/power, working frequency, pulse frequency, therapy cycle duration, will be partly automatically recognized by the system as a function of the specific transducer used and partly settable remotely, as will be described below.

It should be noted that, in an embodiment, the device 100 further comprises a respective first pad integral with the at least one low-intensity focused-ultrasound sonication probe SD.

The pad is adapted to be filled with ultrasound liquid (e.g., gel) to allow better mechanical/acoustic coupling between the at least one low-intensity focused-ultrasound sonication probe SD and the patient's skull.

In accordance with an embodiment, in combination with any of the foregoing and shown in the figures, the device 100 comprises at least one localization unit L1 of a cerebral target to be subjected to low-intensity focused-ultrasound neuromodulation.

The at least one localization unit L1 is configured to localize a cerebral target having a set size.

In a first embodiment, shown in the figures, the at least one localization unit L1 is integrated along an arc defined by the shape of the first movable component 2.

In a second embodiment, alternatively to the preceding one, shown with dashed lines in the figures, the at least one localization unit L1 is integrated in the at least one low-intensity focused-ultrasound sonication probe SD of the low-intensity focused-ultrasound neuromodulation module 10.

In a third embodiment, alternatively to the preceding, shown with dashed lines in the figures, the at least one localization unit L1 is integrated along an arc defined by the shape of the first movable component 2 and the device 100 comprises a further localization unit L2 integrated in the at least one low-intensity focused-ultrasound sonication probe SD of the low-intensity focused-ultrasound neuromodulation module 10.

The further localization unit L2 is configured to localize a cerebral target having a set further size.

The at least one localization unit L1, when integrated in the arc along an arc defined by the shape of the first movable component 2 (first and third embodiments described above) is configured to perform functional near-infrared spectroscopy (fNIRS).

In these embodiments, the set size of the cerebral target localizable by the at least one localization unit L1 is less than 1 $cm^3$.

Figure 5:
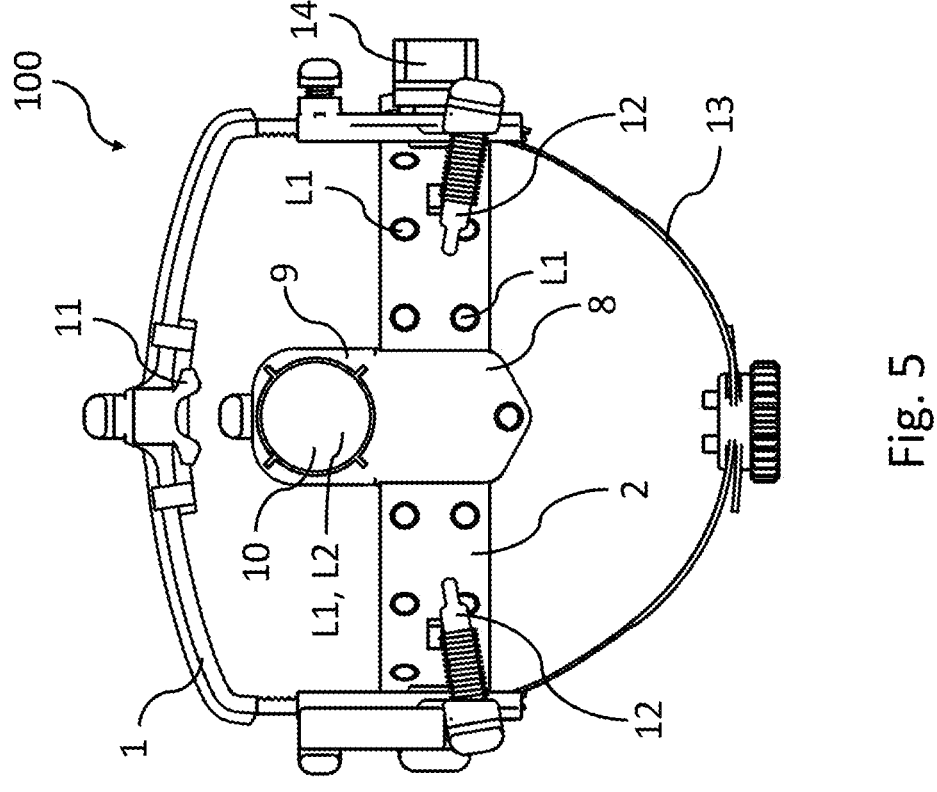
FIG. 5 diagrammatically shows a bottom view of the stereotactic device for low-intensity focused ultrasonic neuromodulation in FIG. 1.
Figure 4:
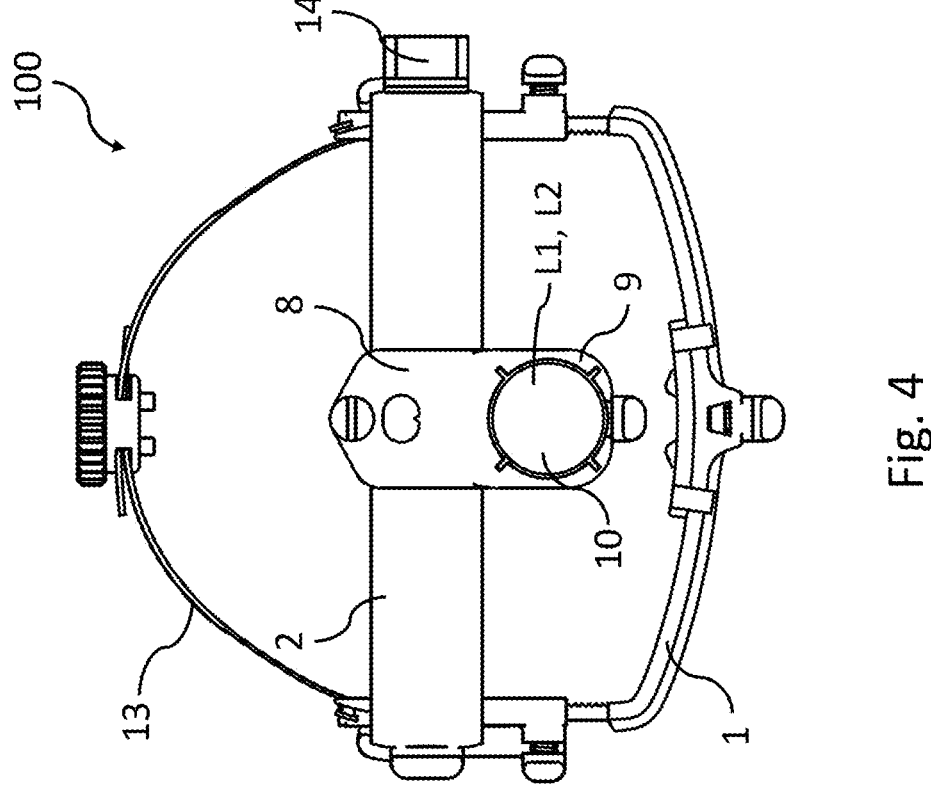
FIG. 4 diagrammatically shows a top view of the stereotactic device for low-intensity focused ultrasonic neuromodulation in FIG. 1.
Figure 9:
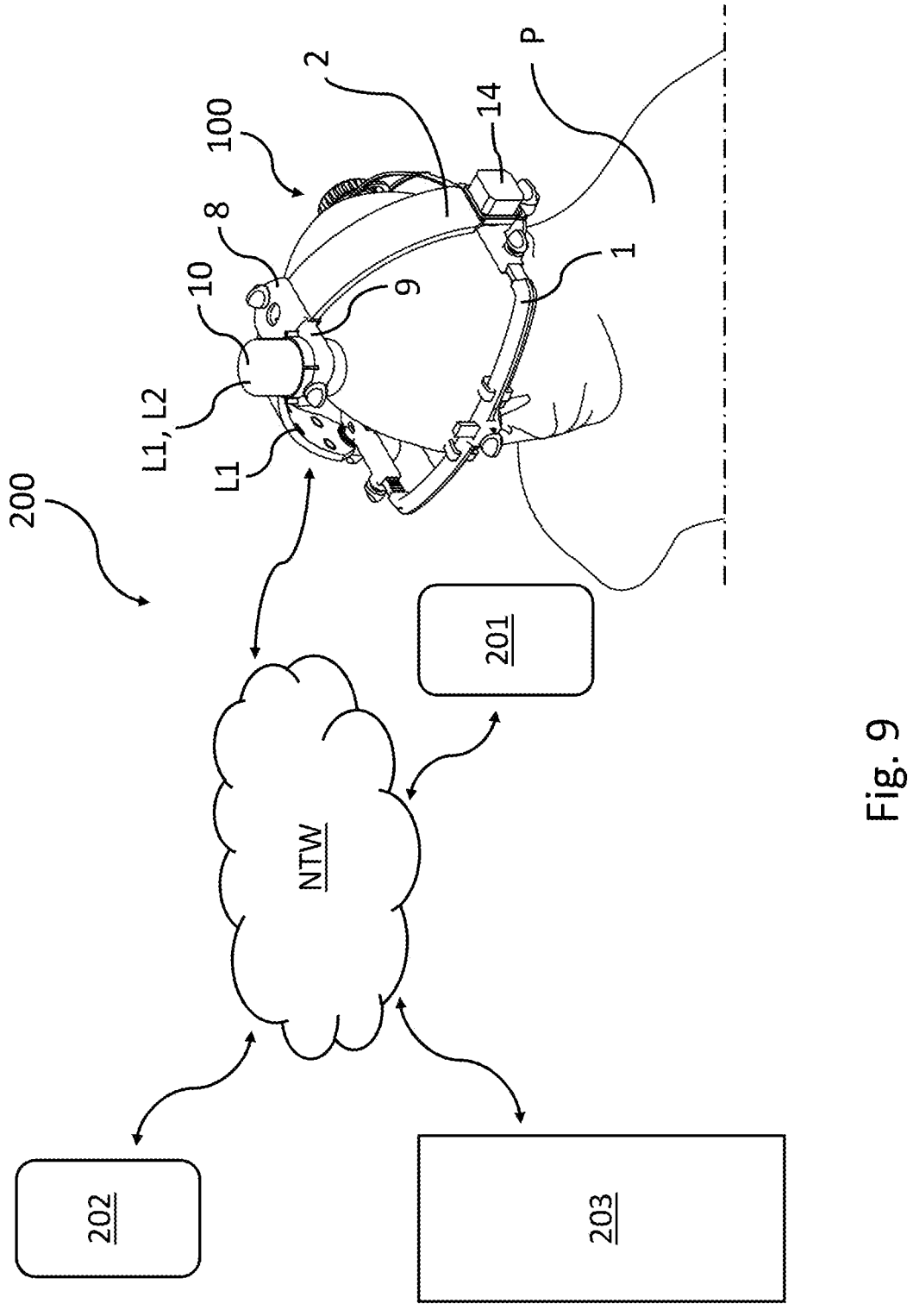
FIG. 9 diagrammatically shows a low-intensity focused-ultrasound neuromodulation system, according to the present invention, adapted to employ the device in FIG. 1.

In these embodiments, the at least one localization unit L1 comprises a plurality of functional near-infrared imaging sensors distributed along the arc defined by the shape of the first movable component 2 (as seen for example in FIGS. 1, 5 and 9).

Functional near-infrared imaging employs near-infrared light, having a wavelength in the interval 650-950 nm.

By means of this technology, the light is sent using a laser through the scalp and skull while a photodiode measures the light after interaction with the brain.

Brain activity induces hemodynamic fluctuations by virtue of the neuro-vascular coupling phenomenon, giving rise to changes in the concentration of oxyhemoglobin (O2Hb) and deoxy-hemoglobin (HHb).

Thereby, these changes can be detected by exploiting the different absorption spectra of oxygenated and deoxygenated hemoglobin.

It should be noted that during the execution of a simple motor task, the at least one localization unit L1, configured to perform functional near-infrared imaging, is configured to provide a real-time image of the cerebral activation spots of the motor and supplementary motor cortices, allowing the identification of three precise intracerebral reference points (landmarks).

This technology is high density (in fact, a high number of photodiodes is included) which advantageously allows a high spatial resolution.

When the localization unit is integrated in the at least one sonication probe CD of the low-intensity focused-ultrasound neuromodulation module 10, either the at least one localization unit L1 (second embodiment described above) or the further one localization unit L2 (third embodiment described above), the localization unit (L1 or L2) is configured to perform diagnostic ultrasonography, so as to provide a real-time image of the position of the two cerebral ventricles for the identification of the cerebral target position having a set size (in the case of the at least one localization unit L1) or a set further size (in the case of the further localization unit L2) greater than 1 cm$^3$.

In these embodiments, the localization unit (L1 or L2) integrated in the at least one low-intensity focused-ultrasound sonication probe SD of the low-intensity focused-ultrasound neuromodulation module 10 is a two-dimensional planar wave ultrasound (US) localizer.

Figure 6B:
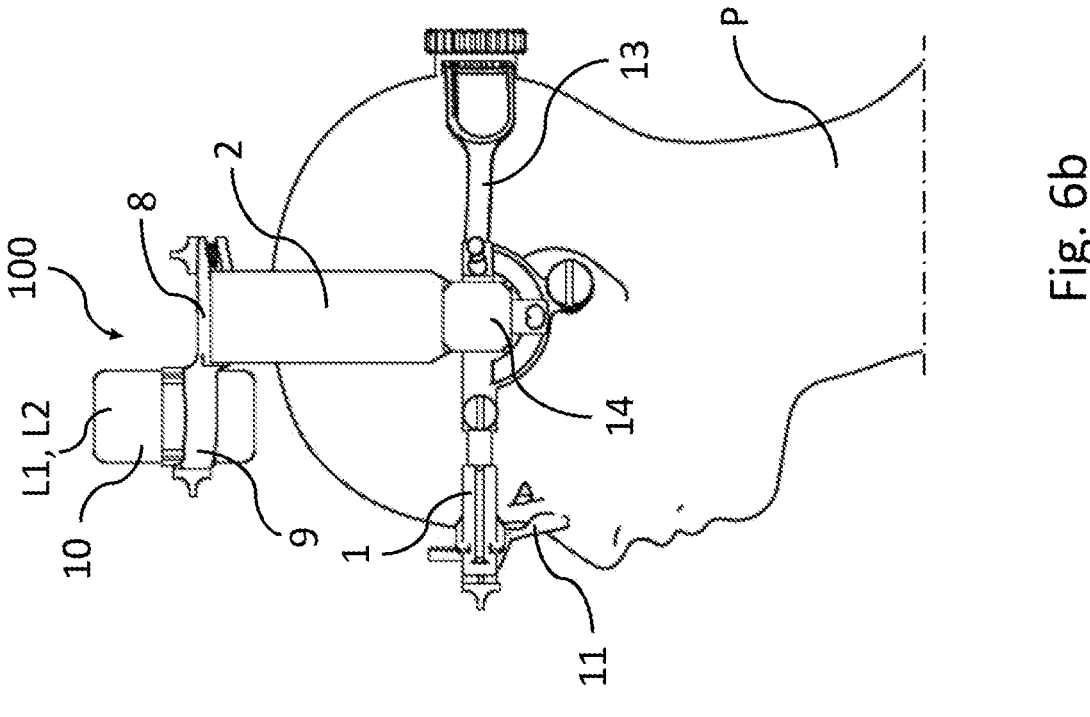
FIGS. 6a and 6b diagrammatically show a front view and a side view, respectively, of the stereotactic device for low-intensity focused-ultrasound neuromodulation in FIG. 1 when worn by a patient, in a first operating configuration.
Figure 6A:
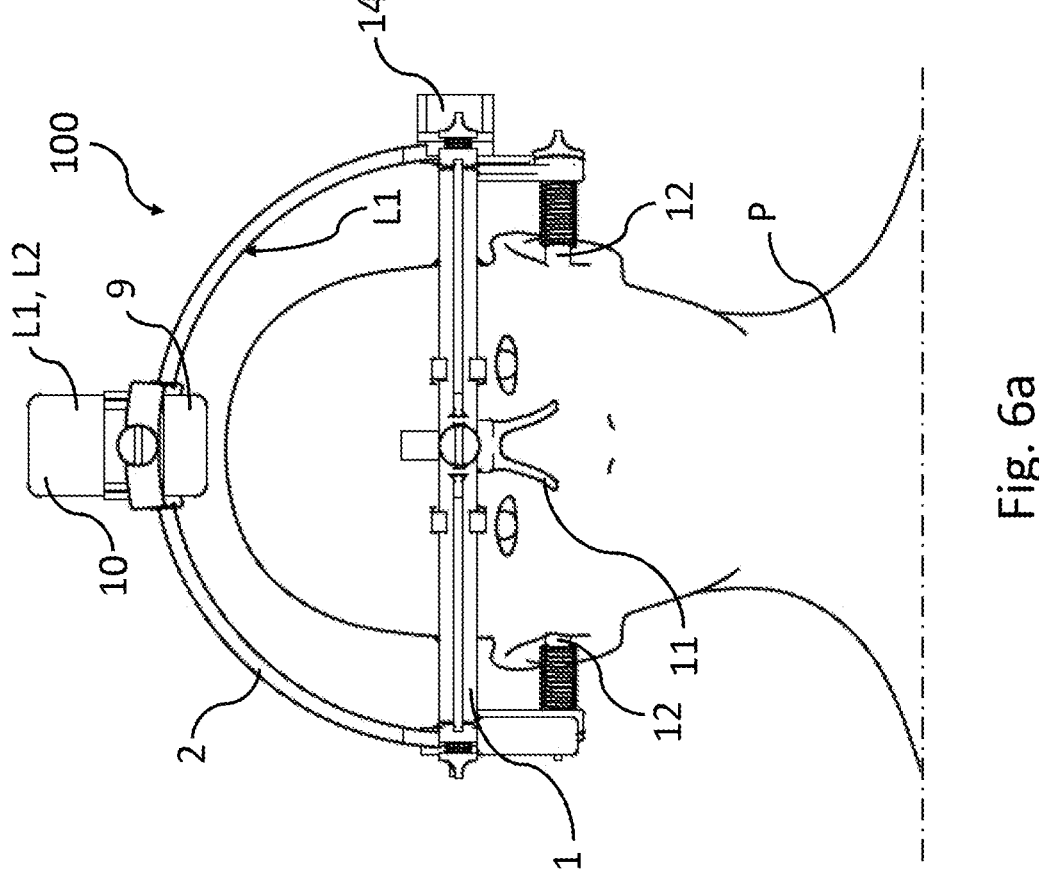
Figures 7A, 7B:
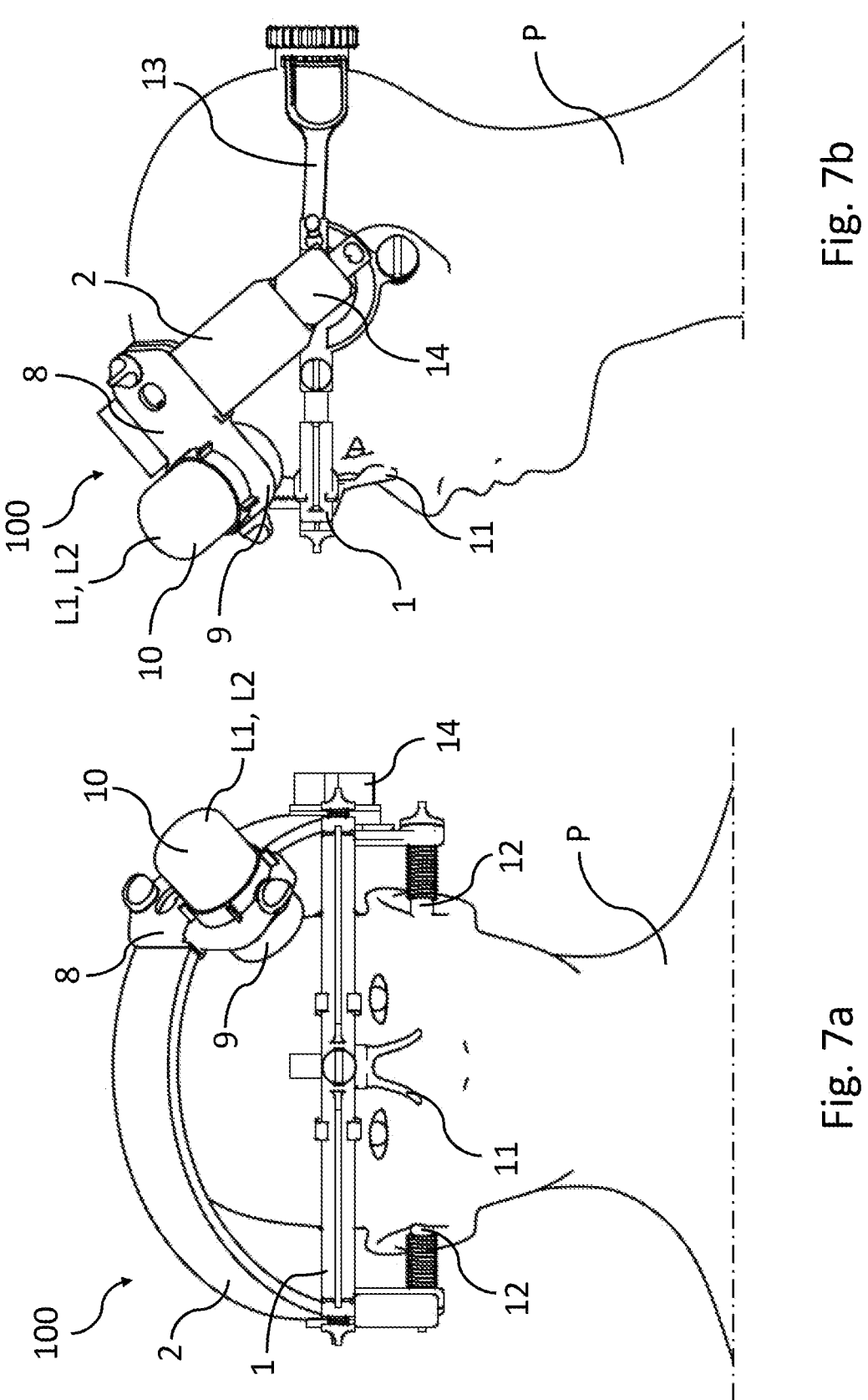
FIGS. 7a and 7b diagrammatically show a front view and a side view, respectively, of the stereotactic device for low-intensity focused-ultrasound neuromodulation in FIG. 1 when worn by a patient, in a second operating configuration.

In an embodiment, in combination with any of those described above and shown in the figures, in order to allow the device 100 to be wearable by a patient P, the device 100 comprises a nasal support 11 operatively associated with the support frame 1 to secure the support frame 1 to a midpoint of the nasal-frontal suture of the head of the patient P (see for example FIGS. 6a and 7a).

In a further embodiment, shown in FIGS. 1, 2, 3, 4, 5, 6b and 7b, the device 100 comprises a rear support 13 operatively connected to the support frame 1 at the first 5 and second 6 coupling points of the support frame 1 in which the first movable component 2 is engaged with the support frame 1.

In a further embodiment, shown in FIGS. 1, 2, 3, 4, 5, 6b and 7b, the device 100 comprises a rear support 13 operatively connected to the support frame 1 at the first 5 and second 6 coupling points of the support frame 1 in which the first movable element 2 is engaged with the support frame 1.

The rear support 13 is for example an adjustable strap around the occipital region of the head of the patient P.

Figure 8:
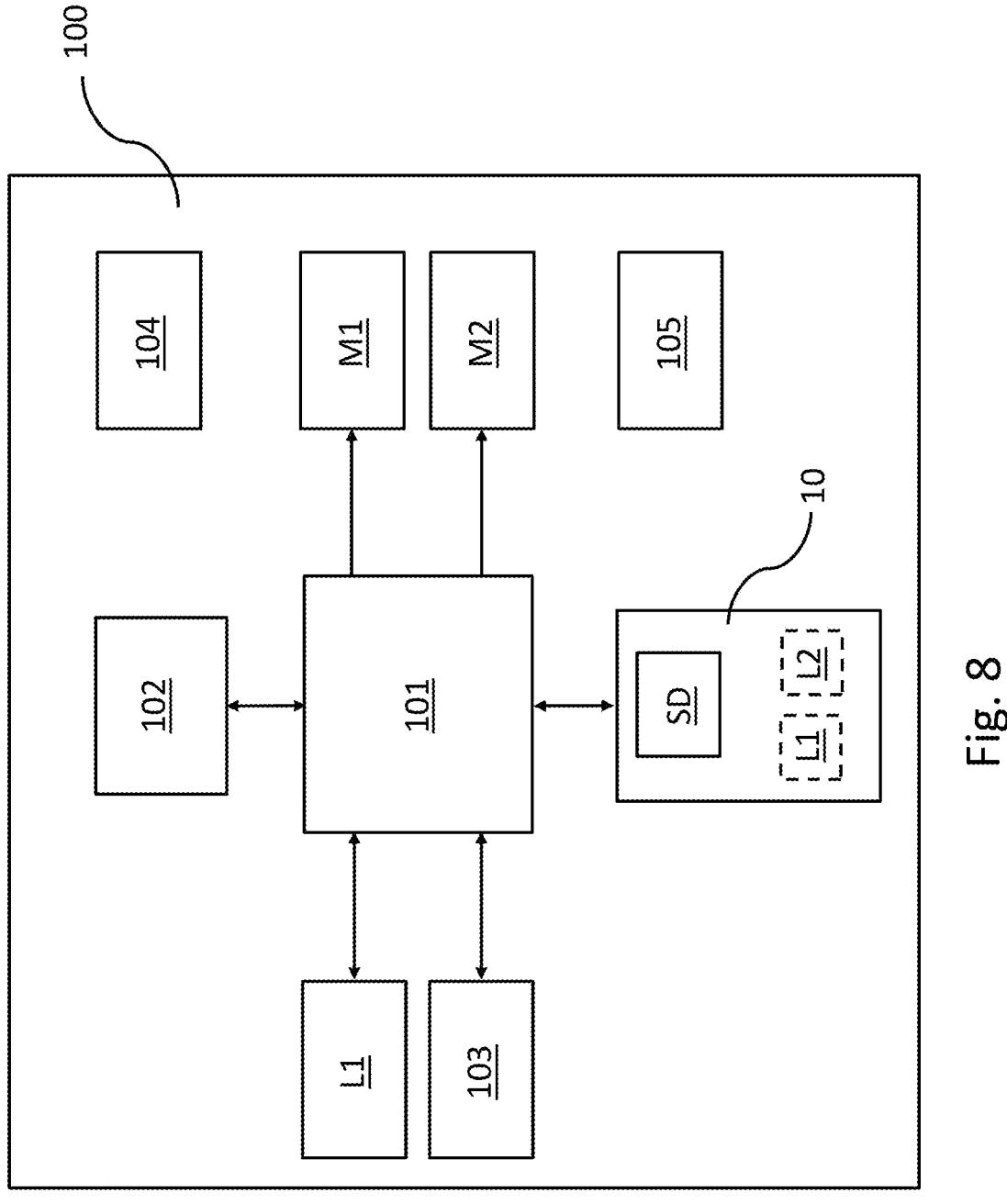
FIG. 8 shows, by means of a block diagram, a stereotactic device wearable by a patient for low-intensity focused-ultrasound neuromodulation, according to an embodiment of the present invention.

From a functional point of view, with particular reference to FIG. 8, in accordance with an embodiment in combination with any one of the preceding ones, the device 100 comprises a local data processing unit 101, for example, a microcontroller or a microprocessor.

The device 100 further comprises a local memory unit 102, operatively connected to the respective local data processing unit 101.

The local memory unit 102 can be internal or external (for example as shown in FIG. 8) to the local data processing unit 101.

It should be noted that the local memory unit 102 is configured to store one or more program codes executable by the local data processing unit 101 and the data generated and processed following the execution of said one or more program codes.

The data processing unit 101 is configured to control the operation of the device 100, as will be described below.

As shown in FIG. 8, the device 100 comprises a first servo-assisted motorization unit M1 configured to rotate the first movable component 2 with respect to the support frame 1.

The local data processing unit 101 is operatively connected to the first servo-assisted motorization unit M1.

Furthermore, the device 100 comprises a second servo-assisted motorization unit M2 (also diagrammatically shown in FIG. 8) configured to slide the second movable component 7 along the first movable component 2.

The local data processing unit 101 is operatively connected to the second servo-assisted motorization unit M2.

As also shown in FIG. 8, the device 100 further comprises a low-intensity focused-ultrasound neuromodulation module 10.

The local data processing unit 101 is operatively connected to the low-intensity focused-ultrasound neuromodulation module 10.

The local data processing unit 101 is operatively connected to the at least one low-intensity focused-ultrasound sonication probe SD of the low-intensity focused-ultrasound neuromodulation module 10.

Furthermore, the local data processing unit 101 is operatively connected to the at least one localization unit L1 either the at least one localization unit L1 integrated in the arc defined by the shape of the first movable component 2 or the at least one further localization unit L1 integrated in the low-intensity focused-ultrasound neuromodulation module 10.

Furthermore, in an embodiment, in which the device 100 comprises the at least one localization unit L1 and the further localization unit L2 of a cerebral target to be subjected to low-intensity focused-ultrasound neuromodulation, the local data processing unit 101 is operatively connected to the at least one localization unit L1 of cerebral targets and to the further localization unit L2 of cerebral targets.

Still with reference to FIG. 8, in an embodiment, the device 100 further comprises a data communication module 103 operatively connected to the local data processing unit 101.

The data communication module 103 is configured to wirelessly communicate real-time data with electronic devices, described below with reference to FIG. 9.

In greater detail, the data communication module 103 is configured both to communicate real-time data wirelessly, employing a wireless technology such as Wi-Fi, Bluetooth, NFC, and so on, thus with electronic devices near and/or close to the device 100 and to communicate real-time data wirelessly using a data communication network, for example the Internet, thus with remote electronic devices with respect to the device 100.

As will be described below, the data communication module 103 is configured to allow the local data processing unit 101 to send and receive data during the preparation of the device 100 for the operation thereof and during the operation of the device 100.

Returning to FIG. 8, the device 100 further comprises an electric power supply module 104, for example a battery, operatively connected to the electrical/electronic components with which the device 100 is provided.

The electric power supply module 104 is configured to provide electric power for a set time duration, e.g., at least 4 hours.

It should be noted that at least the local data processing unit 101, the local memory unit 102, the data communication module 103 and the at least one power supply module 104 are housed inside a respective housing 14 of the device 100, for example associated with the first movable component 2 (as diagrammatically shown in the figures).

In an embodiment, shown with dashed lines in FIG. 8, the device 100 further comprises at least one hydraulic pump 105 operatively connected to each of the pads integral with the low-intensity focused-ultrasound neuromodulation module 10 and with the at least one cerebral target localization unit L1 (and the further localization unit L2, if present).

The hydraulic pump 105 is automatically operable prior to the start of cerebral target localization and sonication procedures to fill the pad with liquid (e.g., gel) for ultrasound.

With reference now also to FIG. 9, a low-intensity focused-ultrasound (LIFU) neuromodulation system 200 is now described, hereinafter also referred to as neuromodulation system or simply system 200.

The system 200 comprises the stereotactic device 100, wearable by a patient, for low-intensity focused-ultrasound neuromodulation, according to any one of the embodiments described above.

The system 200 further comprises a first electronic device 201 configured to be operatively connected to the device 100.

In greater detail, the first electronic device 201 is configured to be wirelessly connected, employing wireless technology such as Wi-Fi, Bluetooth, NFC, and so on, to the device 100.

The first electronic device 201 is near and/or close to the device 100.

The first electronic device 201 is for example a mobile phone (smartphone), a tablet, a notebook, a personal computer of the patient P in possession of the device 100 or of a relative or other person responsible for the patient P.

As will be described below, the first electronic device 201 is configured to store and execute one or more program codes or software applications executable by the first electronic device 201 during the preparation of the device 100 for the operation thereof and during the operation of the device 100.

Always with reference to FIG. 9, the system 200 further comprises a second electronic device 202 configured to be operatively connected to the device 100.

In greater detail, the second electronic device 202 is configured to be wirelessly connected, employing a data communication network NTW (diagrammatically shown in FIG. 9), e.g., the Internet, to the device 100.

The second electronic device 202 is remote with respect to the device 100.

The second electronic device 202 is for example a mobile phone (smartphone), a tablet, a notebook, a personal computer of a physician or a member of a medical staff.

As will be described below, the second electronic device 202 is configured to store and execute one or more program codes or software applications executable by the second electronic device 202 during the preparation of the device 100 for the operation thereof and during the operation of the device 100.

Always with reference to FIG. 9, the system 200 further comprises a remote electronic computer 203, for example a cloud server.

The first electronic device 201 is configured to be wirelessly connected, using the data communication network NTW, to the remote electronic computer 203.

The second electronic device 202 is also configured to be wirelessly connected, using the data communication network NTW, to the remote electronic computer 203.

The remote electronic computer 203 is configured to store and execute one or more program codes or software applications executable by the remote electronic computer 203 during the preparation of the device 100 for the operation thereof and during the operation of the device 100.

The remote electronic computer 203 is configured to store (and co-record) images representative of preparatory medical examinations performed on the patient P.

Such medical examinations are preparatory for the subsequent preparation for the operation of the device 100 and the operation of the device 100, as will be described below.

Such medical examinations comprise, for example, functional magnetic resonance imaging (fMRI), structural magnetic resonance imaging (RM), functional near-infrared imaging (fNIRS), computed tomography (CT).

In greater detail, the images representative of preparatory medical examinations performed on the patient P are stored in the remote electronic computer 203 prior to the low-intensity focused-ultrasound neuromodulation session.

To this end, operations are included such as acquisition, processing and recording of data from different imaging techniques such as functional magnetic resonance imaging (fMRI) during the execution, by the patient P, of a finger-tapping exercise, structural magnetic resonance imaging (RM), functional near-infrared imaging (fNIRS) during the execution, by the patient P, of a finger-tapping exercise, computed tomography (CT) for the evaluation of the thickness of the skull (to be used for the calculation of sonication parameters, defined below).

Such exams allow obtaining a low-intensity ultrasound neuromodulation reproducible over time through an automated identification of the stereotactic coordinates of the cerebral target before stimulation with low-intensity focused-ultrasound neuromodulation.

Returning to the first electronic device 201, it is configured to perform an automatic data connection with the data communication module 103 of the device 100.

This automatic data connection (synchronization) occurs by employing the most suitable wireless technology available (for example, Bluetooth, Wi-Fi, NFC, etc.).

The first electronic device 201 is configured to verify the state of psycho-physical, neurophysiological, neuropsychological and psychiatric well-being of the patient P in relation to the disease to be treated and for the evaluation of any contraindications in performing the low-intensity focused-ultrasound neuromodulation session.

In this regard, the first electronic device 201 is configured to perform the aforesaid verification by having the patient P perform different types of tests (neurophysiological, neuropsychological and neuropsychiatric).

The first electronic device 201 is configured to verify whether the values emerged from the tests performed by the patient P fall within permitted ranges of values and, if so, the first electronic device 201 is configured to authorize the patient P to wear the device 100.

The first electronic device 201 is configured, once the device 100 is fitted on the head of the patient P in a neutral position (first movable component 2 inclined with respect to the reference plane PR by a set angle substantially equal to) 90°, to identify the position of the device 100 as a reference coordinate system.

Furthermore, the first electronic device 201 is configured to determine stereotactic coordinates of intracerebral reference points (landmarks) or cerebral ventricles of the patient P with respect to the reference coordinate system corresponding to the position of the device 100.

In a first embodiment, in which the at least one cerebral target localization unit L1 of the device 100 (integrated in the arc defined by the shape of the first movable component 2) is configured to perform functional near-infrared imaging (fNIRS), the first electronic device 201 is configured to process fNIRS data received from the at least one localization unit L1 in real time to functionally identify fNIRS signal peaks during the execution, by the patient P, of a finger-tapping task.

In this first embodiment, the first electronic device 201 is configured to determine the stereotactic coordinates of the cerebral reference points (landmarks) with respect to the reference coordinate system corresponding to the position of the device 100, based on the comparison between the fNIRS signal peaks identified with the signal peaks obtained from the images representative of prepared medical examinations (fMRI and fNIRS performed in the preparatory step) performed by the patient P stored in the remote electronic computer 203.

In a second embodiment, in which a cerebral target localization unit of the device 100 (either the at least one localization unit L1 or the at least one further localization unit L1 integrated in the at least one low-intensity focused-ultrasound sonication probe SD) is configured to perform diagnostic ultrasonography (US), the first electronic device 201 is configured to process US images received from the localization unit L1 or L2 in real time to identify cerebral ventricles of the patient P.

In this second embodiment, the first electronic device 201 is configured to determine the stereotactic coordinates of the cerebral ventricles of the patient P with respect to the reference coordinate system corresponding to the position of the device 100, based on the comparison between the received US images and the images representative of prepared medical examinations performed by the patient P stored in the remote electronic computer 203.

Returning in general to the first electronic device 201, it is configured to send to the remote electronic computer 203 the stereotactic coordinates of intracerebral reference points (landmarks) (first embodiment with functional near-infrared imaging fNIRS) or cerebral ventricles (second embodiment with diagnostic ultrasonography US) of the patient P determined with respect to the reference coordinate system corresponding to the position of the device 100.

The remote electronic computer 203 is configured to determine the stereotactic coordinates of the cerebral target to be subjected to low-intensity focused-ultrasound neuromodulation, thereby the spatial coordinates on which to target a low-intensity focused-ultrasound neuromodulation beam, with respect to the stereotactic coordinates of intracerebral reference points (landmarks) or cerebral ventricles of the patient P received by the first electronic device 201.

In a first embodiment, the remote electronic computer 203, with extreme precision, by virtue of the cross-correlation between the identified fNIRS signal peaks (stereotactic coordinates of the cerebral reference points (landmarks) of the patient P) received from the first electronic device 201 and the signal peaks obtained from the images representative of preparatory medical examinations performed by the patient P stored in the remote electronic computer 203, is configured to determine stereotactic coordinates of the cerebral target to be subjected to low-intensity focused-ultrasound neuromodulation and thus the spatial coordinates on which to direct a low-intensity focused-ultrasound neuromodulation beam.

In greater detail, in this first embodiment, the remote electronic computer 203 is configured to determine the stereotactic coordinates of the cerebral target to be subjected to low-intensity focused-ultrasound neuromodulation with respect to the stereotactic coordinates of functional cerebral reference points (landmarks) obtained from the processing of fNIRS data received during the positioning of the device 100 on the head of the patient P.

In a second embodiment, the remote electronic computer 203, with extreme precision, by virtue of the cross-correlation between the received US images (stereotactic coordinates of the cerebral ventricles of the patient P) received from the first electronic device 201 and the images representative of preparatory medical examinations performed by the patient P stored in the remote electronic computer 203, is configured to determine stereotactic coordinates of the cerebral target to be subjected to low-intensity focused-ultrasound neuromodulation and thus the spatial coordinates on which to direct a low-intensity focused-ultrasound neuromodulation beam.

In greater detail, in this second embodiment, the remote electronic computer 203 is configured to determine the stereotactic coordinates of the cerebral target to be subjected to low-intensity focused-ultrasound neuromodulation with respect to the stereotactic coordinates of the cerebral ventricles of the patient P obtained from processing the US data received during the positioning of the device 100 on the head of the patient P.

In accordance with any one of the embodiments above, the remote electronic computer 203 is configured to send to the second electronic device 202 (thus, to the physician) and to the first electronic device 201, the stereotactic coordinates of the cerebral target to be subjected to set low-intensity focused-ultrasound neuromodulation.

With reference now to the second electronic device 202, it is configured to identify a patient P to be subjected to low-intensity focused-ultrasound neuromodulation and a stereotactic device 100 wearable by a patient P for low-intensity focused-ultrasound neuromodulation provided to the identified patient P.

The second remote electronic device 202 is configured to acquire from the remote electronic computer 203 images representative of preparatory medical examinations performed on the patient P.

The second remote electronic device 202 is further configured to aggregate, or overlap, the stereotactic coordinates of the cerebral target to be subjected to low-intensity focused-ultrasound neuromodulation determined with images representative of preparatory medical examinations performed on the patient P acquired by the remote electronic computer 203.

The second electronic device 202 is configured to set sonication parameters of the device 100, such as power and operating frequency.

In an embodiment, if the device 100 has performed low-intensity ultrasound neuromodulation on a cerebral target of the patient P, in order to increase the safety of the device 100, the second electronic device 202 is configured to compare the sonication parameters during the preparation step with previously set sonication parameters.

The second electronic device 202 is configured to send a low-intensity focused-ultrasound neuromodulation command to the device 100.

At the end of the low-intensity focused-ultrasound neuromodulation session, the second electronic device 202 is configured to receive from the first electronic device 201 data related to the state of psycho-physical well-being of the patient P and data representative of the performed low-intensity focused-ultrasound neuromodulation.

Returning to the first electronic device 201, it is further configured to control the rotation of the first movable component 2 about the rotation axis passing through the first 5 and second 6 coupling points of the support frame 1 and to control the sliding of the engagement portion 8 of the second movable component 7 with respect to the first movable component 2 so as to position the low-intensity focused-ultrasound neuromodulation module 10 at the cerebral target identified by the set stereotactic coordinates.

In accordance with an embodiment, the first electronic device 201 is configured to verify, by means of pressure switch control, the correct filling with liquid (gel) for ultrasound, of the pad integral with the low-intensity focused-ultrasound neuromodulation module 10.

It should be noted that the pad is filled automatically, for example by providing the ultrasound liquid (gel) in a container connectable to the hydraulic pump 105 with which the device 100 is provided.

The first electronic device 201 is further configured to send the tests (neurophysiological, neuropsychological and neuropsychiatric) performed by the patient P for the evaluation of the patient P to a physician.

The first electronic device 201 is configured to receive from the physician (i.e., from the second remote electronic device 202) a confirmation of initiation of low-intensity focused-ultrasound neuromodulation.

The first electronic device 201 is configured to control the low-intensity focused-ultrasound neuromodulation, by the at least one low-intensity focused-ultrasound sonication probe SD of the low-intensity ultrasonic neuromodulation module 10, on the cerebral target identified by the set stereotactic coordinates.

The first electronic device 201 is further configured to ask the patient P, at the end of the low-intensity focused-ultrasound neuromodulation session, to perform further tests in order to assess the state of psycho-physical well-being, for example, an MMSE (Mini-Mental State Examination) test, for the evaluation of executive and mnemonic functions.

The first electronic device 201 is configured to send the state of psycho-physical well-being of the patient P and data representative of the low-intensity focused-ultrasound neuromodulation performed to the physician (i.e., the second remote electronic device 202).

Figure 10:
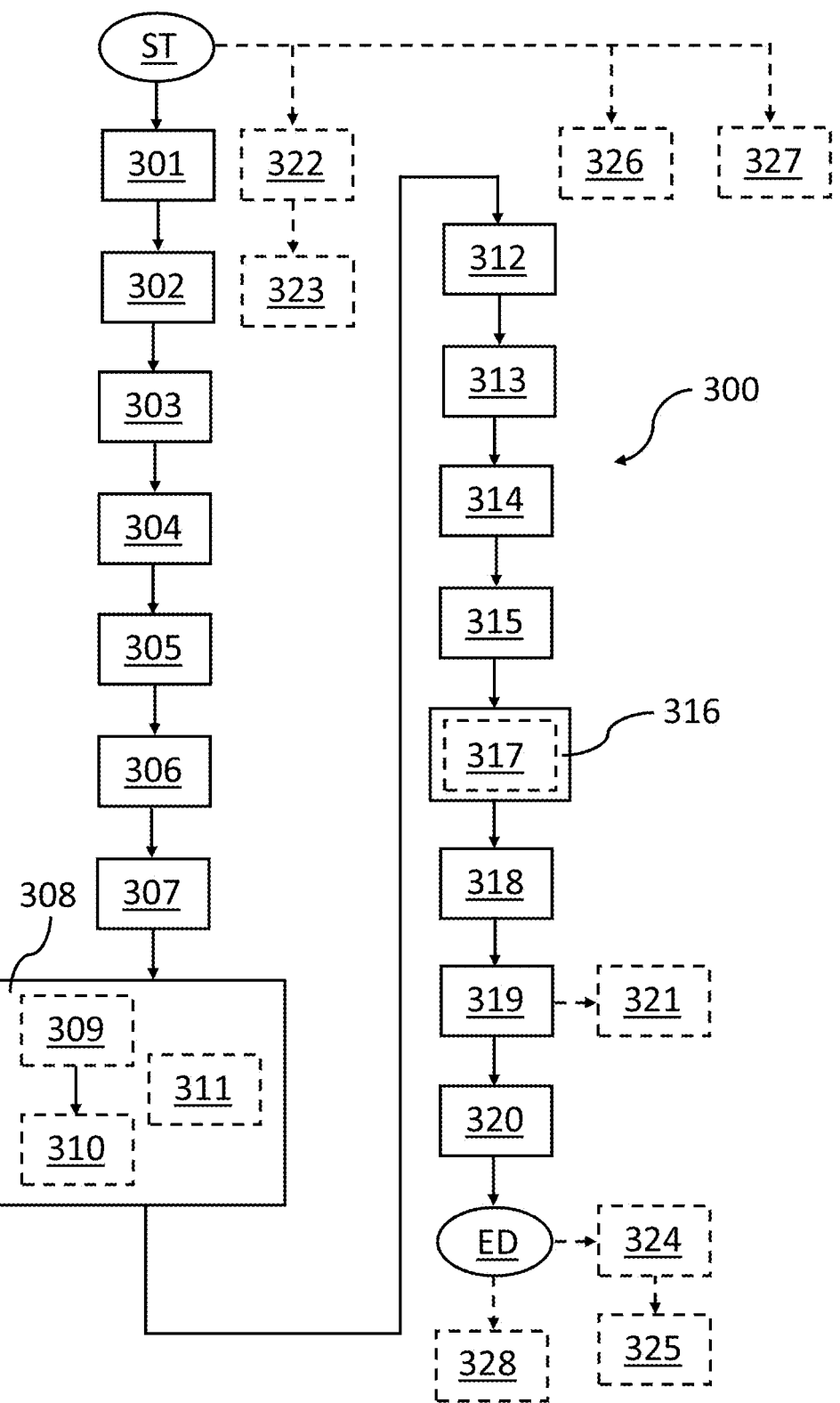
FIG. 10 shows, by means of a block diagram, a low-intensity focused-ultrasound neuromodulation method, in accordance with the present invention, employing the device in FIG. 1.

With reference now also to FIG. 10, a low-intensity focused-ultrasound neuromodulation method 300 is now described.

The method 300 comprises a symbolic step of starting ST.

The method 300 comprises a step of providing 301 a stereotactic device 100, wearable by a patient, for low-intensity focused-ultrasound neuromodulation, according to any one of the embodiments described above.

The method 300 comprises a step of providing 302 a first electronic device 201 configured to be operatively connected to the device 100.

The first electronic device 201 is configured to be wirelessly connected, employing wireless technology such as Wi-Fi, Bluetooth, NFC, and so on, to the device 100.

The first electronic device 201 is near and/or close to the device 100.

Examples of first electronic device 201 have been provided above.

The method 300 further comprises a step of providing 303 a second electronic device 202 configured to be operatively connected to the device 100.

In greater detail, the second electronic device 202 is configured to be wirelessly connected, employing a data communication network NTW, e.g., the Internet, to the device 100.

The second electronic device 202 is remote with respect to the device 100.

Examples of second electronic device 202 have been described above.

The method 300 further comprises a step of providing 304 a remote electronic computer 203, e.g., a cloud server.

The first electronic device 201 is configured to be wirelessly connected, using a data communication network NTW, to the remote electronic computer 203.

The second electronic device 202 is also configured to be wirelessly connected, using the data communication network NTW, to the remote electronic computer 203.

The method 300 comprises a step of storing 305, by the remote electronic computer 203, images representative of preparatory medical examinations performed on the patient P.

Such medical examinations, preparatory for the subsequent preparation for the operation of the device 100 and the operation of the device 100, have been described above.

The method 300 comprises a step of performing 306, by the first electronic device 201, an automatic data connection with a data communication module 103 of the device 100.

The method 300 comprises a step of verifying 307, by the first electronic device 201, a state of psycho-physical, neuropsychological and psychiatric well-being of the patient P.

Methods for verifying the psycho-physical, neurophysiological, neuropsychological and psychiatric well-being of patient P have been described above.

The step of verifying 307 is performed, by the first electronic device 201, to check whether or not the values emerged from the tests performed by the patient P fall within permitted ranges of values and, if so, authorize the patient P to wear the device 100.

Once the device 100 is fitted on the head of the patient P in a neutral position (first movable component 2 inclined with respect to the reference plane PR by a set angle substantially equal to 90°), the method 300 comprises a step of identifying 307, by the first electronic device 201, the position of the device 100 as a reference coordinate system.

The method 300 further comprises a step of determining 308, by the first electronic device 201, stereotactic coordinates of intracerebral reference points (landmarks) or cerebral ventricles with respect to the reference coordinate system corresponding to the position of the device 100.

In a first embodiment, shown with dashed lines in FIG. 10, in which at least one cerebral target localization unit L1 of the device 100 is configured to perform functional near-infrared imaging (fNIRS), the step of determining 308 comprises steps of:

processing 309 in real time, by the first electronic device 201, fNIRS data received from the at least one localization unit L1, to functionally identify fNIRS signal peaks during the performance, by the patient P, of a finger-tapping task;

co-recording and comparing 310 in real time, by the first electronic device 201, the fNIRS signal peaks identified with signal peaks obtained from images representative of preparatory medical examinations performed by the patient P stored in the remote electronic computer 203.

In this first embodiment, the step of determining 308 the stereotactic coordinates of the intracerebral reference points (landmarks) with respect to the reference coordinate system corresponding to the position of the device 100 is performed by the first electronic device 201 based on the comparison between the fNIRS signal peaks identified with the signal peaks obtained from the images representative of prepared medical examinations performed by the patient P stored in the remote electronic computer 203.

In a second embodiment, shown with dashed lines in FIG. 10, in which at least one cerebral target localization unit L1 (integrated in the at least one low-intensity focused-ultra-sound sonication probe SD) of the device 100 is configured to perform diagnostic ultrasonography (US), the step of determining 308 comprises a step of processing 311 in real time, by the first electronic device 201, US images received from the at least one localization unit L1 to identify cerebral ventricles of the patient P.

In this second embodiment, the step of determining 308 the stereotactic coordinates of the patient's cerebral ventricles P with respect to the reference coordinate system corresponding to the position of the device 100 is performed by the first electronic device 201 based on the comparison between the received US images and the images representative of prepared medical examinations performed by the patient P stored in the remote electronic computer 203.

Returning in general to the method 300 in FIG. 10, it comprises a step of sending 312 to the remote electronic computer 203, by the first electronic device 201, the stereotactic coordinates of intracerebral reference points (landmarks) or cerebral ventricles of the patient P determined with respect to the reference coordinate system corresponding to the position of the device 100.

The method 300 further comprises a step of determining 313, by the remote electronic computer 203, the stereotactic coordinates of the cerebral target to be subjected to low-intensity focused-ultrasound neuromodulation, thus the spatial coordinates on which to direct a low-intensity focused-ultrasound neuromodulation beam, with respect to the stereotactic coordinates of intracerebral reference points (landmarks) or cerebral ventricles of the patient P received by the first electronic device 201.

In accordance with an embodiment, the step of determining 313 is performed, by the remote electronic computer 203, by cross-correlating the identified fNIRS signal peaks (stereotactic coordinates of the cerebral reference points (landmarks) of the patient P) received from the first electronic device 201 and the signal peaks obtained from the images representative of preparatory medical examinations performed by the patient P stored in the remote electronic computer 203, determining the stereotactic coordinates of the cerebral target to be subjected to low-intensity focused-ultrasound neuromodulation with respect to the stereotactic coordinates of functional cerebral reference points (landmarks) obtained from processing the fNIRS data received during the positioning of the device 100 on the head of the patient P.

In accordance with a further embodiment, alternative to the preceding one, the step of determining 313 is performed, by the remote electronic computer 203, by virtue of the cross-correlation between the received US images (stereotactic coordinates of the cerebral ventricles of the patient P) received from the first electronic device 201 and the images representative of preparatory medical examinations performed by the patient P stored in the remote electronic computer 203, determining the stereotactic coordinates of the cerebral target to be subjected to low-intensity focused-ultrasound neuromodulation with respect to the stereotactic coordinates of the cerebral ventricles of the patient P obtained by processing the US data received during the positioning of the device 100 on the head of the patient P.

Returning in general to the method 300 in FIG. 10, it comprises a step of sending 314 to the second electronic device 202 and the first electronic device 201, by the remote electronic computer 203, the stereotactic coordinates of the cerebral target to be subjected to low-intensity focused-ultrasound neuromodulation determined with respect to cerebral reference points (landmarks) obtained from processing the fNIRS data received during the positioning of the device 100 on the head of the patient P or with respect to cerebral ventricles obtained from processing the US data received during the positioning of the device 100 on the head of the patient P.

The method 300 further comprises a step of aggregating 315, by the second remote electronic device 202, the stereotactic coordinates of the cerebral target to be subjected to low-intensity focused ultrasound neuromodulation identified with images representative of preparatory medical examinations performed on the patient P acquired by the remote electronic computer 203.

The method 300 further comprises a step of setting 316, by the second electronic device 202, sonication parameters of the device 100.

In an embodiment, shown with dashed lines in FIG. 10, if the device 100 has previously performed low-intensity ultrasound neuromodulation on a cerebral target of the patient P, the step of setting 316 comprises a step of comparing 317, by the second electronic device 202, the sonication parameters being set with previously set sonication parameters.

Returning in general to the method 300 in FIG. 10, the method 300 further comprises a step of sending 318 to the device 100, by the second electronic device 202, a low-intensity focused ultrasound neuromodulation command.

The method 300 further comprises a step of controlling 319, by the first electronic device 201, the rotation of a first movable component 2 of the device 100 about the rotation axis passing through a first 5 and a second 6 coupling point of a support frame 1 of the device 100 and for controlling the sliding of an engagement portion 8 of a second movable component 7 of the device 100 with respect to the first movable component 2 so as to position a low-intensity focused-ultrasound module 10 of the device 100 at the cerebral target identified by the set stereotactic coordinates.

The method 300 further comprises a step of controlling 320, by the first electronic device 201, low-intensity focused-ultrasound neuromodulation on the cerebral target identified by the set stereotactic coordinates.

The method 300 concludes with a symbolic ending step ED.

In an embodiment, shown with dashed lines in FIG. 10, the method 300 further comprises a step of verifying 321, by the first electronic device 201, by means of pressure switch control, a correct filling with liquid (gel) for ultrasound, of a pad integral with the low-intensity focused-ultrasound neuromodulation module 10.

In an embodiment, shown with dashed lines in FIG. 10, the method 300 further comprises steps of:
    delivering 322, by the first electronic device 201, neuro-physiological, neuropsychological and psychopathological tests for the evaluation of the patient P;

sending 323 to the second electronic device 202 (thus to a physician), by the first electronic device 201, the neurophysiological, neuropsychological and psychopathological tests for the evaluation of the patient P.

In accordance with an embodiment, in combination with any of those described above, shown with dashed lines in FIG. 10, the method 300, at the end of the low-intensity focused-ultrasound neuromodulation session, further comprises steps of:

asking 324 the patient P, by the first electronic device 201, a state of psycho-physical well-being by means of filling in a questionnaire;

sending 325 to the second remote electronic device 202 (thus to the physician), by the first electronic device 201, the state of psycho-physical well-being of the patient P and data representative of the performed low-intensity focused-ultrasound neuromodulation.

In accordance with an embodiment, in combination with any of the foregoing and shown with dashed lines in FIG. 10, the method 300 comprises a step of identifying 326, by the second electronic device 202, a patient P to be subjected to low-intensity focused-ultrasound neuromodulation and a stereotactic device 100 wearable by a patient P for low-intensity focused-ultrasound neuromodulation provided to the identified patient P.

In accordance with an embodiment, shown with dashed lines in FIG. 10, the method 300 further comprises a step of acquiring 327 from the remote electronic computer 203, by the second electronic device 202, images representative of preparatory medical examinations performed on the patient P.

At the end of the low-intensity focused-ultrasound neuromodulation session, the method 300 comprises a step of receiving 328 from the first electronic device 201, by the second electronic device 202, the state of psycho-physical well-being of the patient P and the data representative of the performed low-intensity focused-ultrasound neuromodulation.

With reference to the aforesaid figures, an example of operation of the low-intensity focused-ultrasound neuromodulation system 200 and the stereotactic device 100 wearable by a patient for low-intensity focused-ultrasound neuromodulation is now described.

As preliminary examinations to be carried out only once, following evaluation by the physician and having received the suitability for the low-intensity ultrasound neuromodulation session, the patient P carries out a magnetic resonance imaging (RM) comprising a structural sequence (T1-weighted) and a computed tomography (CT) scan wearing the device 100 in a neutral position (support frame 1 resting on the reference points (landmarks) of the head of the patient P and first movable component 2 positioned at 90 degrees with respect to the reference plane PR, see for example FIGS. 6a and 6b).

In case of localization of a cerebral target during sonication sessions through functional near-infrared imaging (fNIRS) (cerebral target with a set size less than 1 cm³), the patient P also carries out a functional magnetic resonance imaging (fMRI) during the execution of a finger-tapping exercise (for example, movement of the thumb only at a frequency of 1 Hz), as a preliminary examination to be performed only once.

In case of localization of the cerebral target through diagnostic ultrasonography (US), the patient P must not carry out any functional magnetic resonance imaging (fMRI).

Images obtained with near-infrared functional imaging (fNIRS) or with diagnostic ultrasonography US, obtained during the sonication sessions are co-recorded and stored in the remote electronic computer 203 with the structural image obtained with structural magnetic resonance RM (T1-weighted).

If a functional magnetic resonance imaging (fMRI) was also acquired during the execution of a finger-tapping exercise, such an image will be previously co-recorded with the structural magnetic resonance RM (T1-weighted).

The images representative of the preparatory medical examinations performed by the patient P are stored automatically by the remote electronic computer 203 (cloud).

In this preliminary step, under direct medical supervision, the cerebral target to be subjected to low-intensity focused-ultrasound neuromodulation is identified and defined based on stereotactic coordinates in relation to the reference coordinate system corresponding to the position of the device 100.

In greater detail, during the sonication sessions, the localization is carried out with functional near-infrared imaging (fNIRS) or with diagnostic ultrasonography US of the cerebral target to be subjected to low-intensity focused-ultrasound neuromodulation before the low-intensity focused-ultrasound (LIFU) sonication.

If the at least one localization unit L1 is configured to perform functional near-infrared imaging (fNIRS), the patient P wears the device 100 in the neutral position and such imaging is performed during the execution of a finger tapping exercise (only thumb at 1 Hz).

The exercise is indicated to the patient P by means of the first electronic device 201, in local mode.

If the at least one localization unit L1 is configured to perform a diagnostic ultrasonography (US), the patient P wears the device 100 in a neutral position and the at least one localization unit L1 acquires a two-dimensional image of the position of the cerebral ventricles.

The first electronic device 201 processes and co-records the data obtained from the fNIRS location or US location and with images representative of preparatory medical examinations stored in the remote electronic computer 203 and identifies the position of the device 100 as a reference coordinate system and determines the stereotactic coordinates of intracerebral reference points (landmarks) or cerebral ventricles of the patient P with respect to the reference coordinate system corresponding to the position of the device 100.

By means of the first electronic device 201, the patient:

fills in a questionnaire related to psycho-physical well-being and evaluation of any contraindications in carrying out a low-intensity focused-ultrasound neuromodulation session;

performs neurophysiological, neuropsychological and psychopathological tests, attesting to the psycho-physical well-being of the patient P.

If the values emerged from the tests performed by the patient P fall inside or outside the permitted ranges, the first electronic device 201 authorizes the patient P to proceed.

At this point, the patient P wears the device 100 in the neutral position.

Upon turning on the wireless connection, for example in Bluetooth technology, the device 100 connects to the first electronic device 201.

If the at least one localization unit L1 is configured to perform functional near-infrared imaging (fNIRS), the first electronic device 201 automatically launches the finger-tapping exercise and the patient P performs the hand movement based on the instructions presented by the first electronic device 201 (and the related software application).

The at least one localization unit L1 acquires the data during the execution of the finger tapping exercise by the patient P and these are transferred in real time to the first electronic device 201 which, in turn, sends the data to the remote electronic computer 203 to co-record and compare signal peaks of the fNIRS data with signal peaks obtained from the images representative of prepared medical examinations performed by the patient P stored in the remote electronic computer 203.

If the at least one localization unit L1 is configured to perform diagnostic ultrasonography (US), the at least one localization unit L1 acquires US images and sends them to the first electronic device 201 which in turn sends them to the electronic computer for co-recording and comparison with images representative of prepared medical examinations performed by the patient P stored in the remote electronic computer 203.

The first electronic device 201 determines the stereotactic coordinates of intracerebral reference points (landmarks) or cerebral ventricles of the patient P with respect to the reference coordinate system corresponding to the position of the device 100 and sends such stereotactic coordinates to the remote electronic computer 203.

The remote electronic computer 203, by virtue of the cross-correlation between the stereotactic coordinates of the intracerebral reference points (landmarks) or cerebral ventricles of the patient P received from the first electronic device 201 and the images representative of preparatory medical examinations performed by the patient P stored in the remote electronic computer 203, is configured to determine stereotactic coordinates of the cerebral target to be subjected to low-intensity focused-ultrasound neuromodulation and thus the spatial coordinates on which to direct a low-intensity focused-ultrasound neuromodulation beam.

The remote electronic computer 203 sends the stereotactic coordinates of the cerebral target to be subjected to low-intensity focused-ultrasound neuromodulation to the second electronic device 202 and the first electronic device 201.

The second electronic device 202 sends a low-intensity focused-ultrasound neuromodulation command to the device 100.

The first electronic device 201 controls the rotation of the first movable component 2 about the rotation axis passing through the first 5 and second 6 coupling points of the support frame 1 and controls the sliding of the engagement portion 8 of the second movable component 7 with respect to the first movable component 2 so as to position the low-intensity focused-ultrasound neuromodulation module 10 at the cerebral target identified by the set stereotactic coordinates.

After remote verification, the physician, by means of the second electronic device 202, sends a low-intensity focused-ultrasound neuromodulation start command by means of the respective module 10 of the device 100 (low-intensity focused-ultrasound sonication probe SD).

As can be seen, the object of the present invention is fully achieved.

The stereotactic device of the present invention comprises a support portion 9 of the low-intensity ultrasonic neuromodulation module 10 which is integral with the engagement portion 8 of the second movable component 7 with the first movable component 2 and extends away from the first movable component 2 transversely to a second reference plane PR' on which the arched shape of the first movable component 2 lies.

Thereby, the low-intensity ultrasound neuromodulation module 10 is located next to the first movable component 2 of the device 100 so that it can be, like the first movable component 2, closer to the head of the patient P, thus to the cerebral target to be subjected to low-intensity focused-ultrasound neuromodulation.

Thereby, the device 100 is more comfortable for the patient, taking up less space, and at the same time ensures a more precise and accurate positioning of the low-intensity focused-ultrasound source with respect to the cerebral target to be subjected to neuromodulation.

The device 100 advantageously integrates low-intensity ultrasound neuromodulation transducers and at least one localization unit configured to perform high-intensity functional near-infrared imaging (fNIRS) or diagnostic ultrasonography (US).

Furthermore, the device 100 is advantageously configured to be wirelessly connectable (e.g., in Bluetooth, Wi-Fi technology, etc.) with a first electronic device (e.g., a smartphone) on which a software application is executable for the complete automation of the movement of the mechanics of the device 100 and the operation thereof, the identification of the cerebral target to be subjected to low-intensity focused-ultrasound neuromodulation, and the release of the low-intensity focused-ultrasound neuromodulation according to set protocols.

A software application installed on a second electronic device (e.g., a smartphone) of the physician advantageously allows the physician to remotely verify and approve the setting and execution of the low-focused-ultrasound neuromodulation.

The device 100 advantageously allows low-intensity focused-ultrasound neuromodulation with high spatial resolution on deep and superficial cerebral targets, allowing a fundamental step in the direction of neuromodulation portability and repeatability.

Its use even in acute settings could have a great impact in determining the course of diseases such as head trauma and stroke.

Finally, since the device 100 requires very little human intervention, it can be used not only by non-specialist medical staff but also by nursing staff and by the patient himself/herself even in non-specialist environments.

In order to meet contingent needs, those skilled in the art can make changes and adaptations to the above-described embodiments of the device or can replace elements with others which are functionally equivalent, without departing from the scope of the following claims. Each of the features described as belonging to a possible embodiment can be achieved irrespective of the other embodiments described.

What is claimed is:

1. A stereotactic device wearable by a patient for low-intensity focused-ultrasound neuromodulation, said stereotactic device comprising:

a support frame extending along a first reference plane, said support frame being shaped to be fitted around a head of the patient;

a first movable component with respect to the support frame, said first movable component having an arched shape that extends upwards with respect to the first reference plane and lies on a second reference plane, the first movable component having a first end and a second end, each end respectively engaged with the support frame in a respective first coupling point and second coupling point, the first movable component being adapted to rotate about a rotation axis passing through the first and second coupling points of the support frame to take a plurality of inclined positions with respect to the first reference plane between a first position in which the first movable component is inclined with respect to the first reference plane by a substantially null angle and a second position in which the first movable component is inclined with respect to the first reference plane by an angle substantially equal to 180°;

a second movable component with respect to the first movable component, the second movable component comprising an engagement portion with the first movable component adapted to allow the second movable component to move integrally with the first movable component, the engagement portion of the second movable component with the first movable component being further adapted to allow the second movable component to slide along the first movable component so as to take a plurality of positions between a first position in which the second movable component is proximal to the first end of the first movable component and a second position in which the second movable component is proximal to the second end of the first movable component, the second movable component further comprising a support portion integral with the engagement portion, said support portion extending away from the first movable component transversely to the second reference plane on which the arched shape of the first movable component lies;

a low-intensity focused-ultrasound neuromodulation module housed in the support portion of the second movable component, said low-intensity focused-ultrasound neuromodulation module being located next to the first movable component of the device, said low-intensity focused-ultrasound neuromodulation module comprising at least one low-intensity focused-ultrasound sonication probe, during sliding of the second movable component along the first movable component, the low-intensity focused-ultrasound neuromodulation module is being adapted to take a plurality of operating positions between a first operating position when the second movable component is proximal to the first end of the first movable component and a second operating position when the second movable component is proximal to the second end of the first movable component.

2. The stereotactic device of claim 1, further comprising at least one localization unit of a cerebral target to be subjected to the low-intensity focused-ultrasound neuromodulation, the at least one localization unit being configured to localize a cerebral target having a set size.

3. The stereotactic device of claim 2, wherein the at least one localization unit is integrated along an arc defined by the arched shape of the first movable component, the at least one localization unit being configured to perform functional near-infrared imaging, the set size localizable by the at least one localization unit being less than 1 cm³.

4. The stereotactic device of claim 3, wherein the at least one cerebral target localization unit comprises a plurality of functional near-infrared imaging sensors distributed along the arc defined by the arched shape of the first movable component.

5. The stereotactic device of claim 2, wherein the at least one localization unit is integrated in the at least one low-intensity focused-ultrasound sonication probe of the low-intensity focused-ultrasound neuromodulation module, the at least one localization unit being configured to perform a diagnostic ultrasonography, the set size localizable by the at least one localization unit being greater than 1 cm³.

6. The stereotactic device according to of claim 2, wherein the at least one localization unit is integrated along an arc defined by the arched shape of the first movable component, the at least one localization unit being configured to perform functional near-infrared imaging, the set size localizable by the at least one localization unit being less than 1 cm³, the stereotactic device further comprising a further localization unit integrated in the at least one low-intensity focused-ultrasound sonication probe of the low-intensity focused-ultrasound neuromodulation module, the further localization unit being configured to localize targets having a set further size, the further localization unit being configured to perform a diagnostic ultrasonography, the set further size localizable by the further localization unit being greater than 1 cm³.

7. The stereotactic device of claim 1, further comprising a nasal support operatively associated with the support frame to secure the support frame to a midpoint of a nasal-frontal suture of the head of the patient.

8. The stereotactic device of claim 1, further comprising ear supports operatively connected to the first and second ends of the first movable component to secure the stereotactic device to acoustic meatuses of the patient.

9. The stereotactic device of claim 1, further comprising a rear support operatively connected to the support frame at the first and second coupling points of the support frame, wherein the first movable component is engaged with the support frame.

10. The stereotactic device of claim 1, further comprising:

a local data processing unit configured to control operation of the stereotactic device, the local data processing unit being operatively connected to the low-intensity focused-ultrasound neuromodulation module and to the at least one localization unit;

a local memory unit operatively connected to the local data processing unit;

a first servo-assisted motorization unit configured to rotate the first movable component with respect to the support frame, the local data processing unit being operatively connected to the first servo-assisted motorization unit;

a second servo-assisted motorization unit configured to slide the second movable component along the first movable component, the local data processing unit being operatively connected to the second servo-assisted motorization unit;

a data communication module operatively connected to the local data processing unit, the data communication module being configured to communicate real-time data wirelessly with electronic devices; and an electric power supply module.

11. The stereotactic device of claim 10, wherein the at least one localization unit is integrated along an arc defined by the arched shape of the first movable component, the at least one localization unit being configured to perform functional near-infrared imaging, the set size localizable by the at least one localization unit being less than 1 cm³, the stereotactic device further comprising a further localization unit integrated in the at least one low-intensity focused-ultrasound sonication probe of the low-intensity focused-ultrasound neuromodulation module, the further localization unit being configured to localize targets having a set further size, the further localization unit being configured to perform a diagnostic ultrasonography, the set further size localizable by the further localization unit being greater than 1 cm$^3$, and wherein the local data processing unit is operatively connected to the further localization unit.

12. The stereotactic device of claim 10, wherein the data communication module is configured both to communicate the real-time data wirelessly with the electronic devices near and/or close to the stereotactic device and to communicate the real-time data wirelessly using a data communication network with remote electronic devices with respect to the stereotactic device.

13. A low-intensity focused-ultrasound neuromodulation system comprising:

the stereotactic device, wearable by a patient, for low-intensity focused-ultrasound neuromodulation, of claim 1;

a first electronic device configured to be operatively connected to the stereotactic device, the first electronic device being configured to be wirelessly connected to the stereotactic device, the first electronic device being near and/or close to the stereotactic device and configured to store and execute one or more program codes or software applications executable by the first electronic device during preparation of the stereotactic device for operation thereof and during the operation of the stereotactic device;

a second electronic device configured to be operatively connected to the stereotactic device, the second electronic device being configured to be connected wirelessly, using a data communication network, to the stereotactic device, the second electronic device being remote from the stereotactic device and configured to store and execute one or more program codes or software applications executable by the second electronic device during preparation of the stereotactic device for operation thereof and during the operation of the stereotactic device; and a remote computer, the first electronic device being configured to be connected wirelessly, using the data communication network, to the remote computer, the second electronic device being configured to be connected wirelessly, using the data communication network, to the remote computer, the remote computer being configured to store images representative of preparatory medical examinations performed on the patient.

* * * * *